US007176161B2

(12) United States Patent
Chu et al.

(10) Patent No.: US 7,176,161 B2
(45) Date of Patent: *Feb. 13, 2007

(54) IMAGING SYSTEM

(75) Inventors: Peter K. Chu, Acton, MA (US); Chien Liu, Wayland, MA (US); Stephen J. Telfer, Arlington, MA (US)

(73) Assignee: Zink Imaging, LLC, Waltham, MA (US)

( * ) Notice: Subject to any disclaimer, the term of this patent is extended or adjusted under 35 U.S.C. 154(b) by 269 days.

This patent is subject to a terminal disclaimer.

(21) Appl. No.: 10/789,648

(22) Filed: Feb. 27, 2004

(65) Prior Publication Data
US 2004/0176248 A1    Sep. 9, 2004

Related U.S. Application Data

(60) Provisional application No. 60/451,208, filed on Feb. 28, 2003.

(51) Int. Cl.
*B41M 5/30* (2006.01)
(52) U.S. Cl. .................. 503/201; 503/200; 503/204
(58) Field of Classification Search ......... 503/200–226
See application file for complete search history.

(56) References Cited

U.S. PATENT DOCUMENTS 4,097,288 A    6/1978  Lawton ........................ 106/21
4,602,263 A    7/1986  Borror et al. ................ 346/201
5,663,115 A    9/1997  Naito et al. .................. 503/201
6,010,808 A    1/2000  Naito et al. ................... 430/19
6,537,410 B2   3/2003  Arnost et al. ................ 156/235

FOREIGN PATENT DOCUMENTS

EP    0 576 015 A1    12/1993
EP    1 234 681 A1    8/2002

OTHER PUBLICATIONS

U.S. Appl. No. 10/789,566, filed Feb. 27, 2004, Cheon et al.
U.S. Appl. No. 10/788,963, filed Feb. 27, 2004, Cheon et al.
U.S. Appl. No. 10/789,276, filed Feb. 27, 2004, Cheon et al.
U.S. Appl. No. 10/789,600, filed Feb. 27, 2004, Allen et al.
U.S. Appl. No. 10/151,432, filed May 20, 2002, Bhatt et al.

*Primary Examiner*—B. Hamilton Hess
(74) *Attorney, Agent, or Firm*—Foley & Lardner LLP; Michel Morency; James F. Ewing

(57) ABSTRACT

There are disclosed imaging members wherein a chemical compound in a crystalline form is converted, at least partially, and preferably substantially completely or completely, to a liquid in the amorphous form, the liquid having intrinsically a different color from the crystalline form. Also described are imaging methods utilizing the imaging members. The conversion of the compound from the crystalline form to the liquid form can be effected by the application of thermal energy or by other imaging techniques.

25 Claims, 3 Drawing Sheets

Colorless    Colored    + NR₃

*Scheme 1*

Colorless    Colored    + NR₃

*Scheme 2*

IMAGING SYSTEM

REFERENCE TO RELATED APPLICATIONS

This application claims the benefit of provisional application Ser. No. 60/451,208, filed Feb. 28, 2003.

This application is related to the following commonly assigned, United States patent applications and patents, the entire disclosures of which are hereby incorporated by reference herein in their entirety:

U.S. patent application Ser. No. 10/789,566, filed on even date herewith;

U.S. patent application Ser. No. 10/788,963, filed on even date herewith;

U.S. patent application Ser. No. 10/789,276, filed on even date herewith;

U.S. patent application Ser. No. 10/789,600, filed on even date herewith;

U.S. patent application Ser. No. 10/151,432, filed May 20, 2002 (U.S. Patent Application Publication No. US2003/0125207 A1); and U.S. Pat. No. 7,537,410 B2.

FIELD OF THE INVENTION

This invention relates to imaging members, imaging methods for forming an image and a method for manufacturing a thermal imaging member and, more particularly, to imaging members and methods wherein formation of an image occurs when a chemical compound in a crystalline form is converted, at least partially, to a liquid, or amorphous, form, the liquid having intrinsically a different color from the crystalline form.

BACKGROUND OF THE INVENTION

The development of thermal print heads (linear arrays of individually-addressable resistors) has led to the development of a wide variety of thermally-sensitive media. In some of these, known as "thermal transfer" systems, heat is used to move colored material from a donor sheet to a receiver sheet. Alternatively, heat may be used to convert a colorless coating on a single sheet into a colored image, in a process known as "direct thermal" imaging. Direct thermal imaging has the advantage over thermal transfer of the simplicity of a single sheet. On the other hand, unless a fixing step is incorporated, direct thermal systems are still sensitive to heat after thermal printing. If a stable image is needed from an unfixed direct thermal system, the temperature for coloration must be higher than any temperature that the image is likely to encounter during normal use. A problem arises in that the higher the temperature for coloration, the less sensitive the medium will be when printed with the thermal print head. High sensitivity is important for maximum speed of printing, for maximizing the longevity of the print head, and for energy conservation in mobile, battery-powered printers. As described in more detail below, maximizing sensitivity while maintaining stability is more easily achieved if the temperature of coloration of a direct thermal medium is substantially independent of the heating time.

Thermal print heads address one line of the image at a time. For reasonable printing times, each line of the image is heated for about ten milliseconds or less. Storage of the medium (prior to printing or in the form of the final image) may need to be for years, however. Thus, for high imaging sensitivity, a high degree of coloration is required in a short time of heating, while for good stability a low degree of coloration is required for a long time of heating.

Most chemical reactions speed up with increasing temperature. Therefore, the temperature required for coloration in the short heating time available from a thermal print head will normally be higher than the temperature needed to cause coloration during the long storage time. Actually reversing this order of temperatures would be a very difficult task, but maintaining a substantially time-independent temperature of coloration, such that both long-time and short-time temperatures for coloration are substantially the same, is a desirable goal that is achieved by the present invention.

There are other reasons why a time-independent coloration temperature may be desirable. It may, for example, be required to perform a second thermal step, requiring a relatively long time of heating, after printing. An example of such a step would be thermal lamination of an image. The temperature of coloration of the medium during the time required for thermal lamination must be higher than the lamination temperature (otherwise the medium would become colorized during lamination). It would be preferred that the imaging temperature be higher than the lamination temperature by as small a margin as possible, as would be the case for time-independent temperature of coloration.

Finally, the imaging system may comprise more than one color-forming layer and be designed to be printed with a single thermal print-head, as described in the above-mentioned patent application Ser. No. 10/151,432. In one embodiment of the imaging system, the topmost color-forming layer forms color in a relatively short time at a relatively high temperature, while the lower layer or layers form color in a relatively long time at a relatively low temperature. An ideal topmost layer for this type of direct thermal imaging system would have time-independent temperature of coloration.

Prior art direct thermal imaging systems have used several different chemical mechanisms to produce a change in color. Some have employed compounds that are intrinsically unstable, and which decompose to form a visible color when heated. Such color changes may involve a unimolecular chemical reaction. This reaction may cause color to be formed from a colorless precursor, the color of a colored material to change, or a colored material to bleach. The rate of the reaction is accelerated by heat. For example, U.S. Pat. No. 3,488,705 discloses thermally unstable organic acid salts of triarylmethane dyes that are decomposed and bleached upon heating. U.S. Pat. No. 3,745,009 reissued as U.S. Reissue Pat. No. 29,168 and U.S. Pat. No. 3,832,212 disclose heat-sensitive compounds for thermography containing a heterocyclic nitrogen atom substituted with an —OR group, for example, a carbonate group, that decolorize by undergoing homolytic or heterolytic cleavage of the nitrogen-oxygen bond upon heating to produce an RO+ ion or RO' radical and a dye base or dye radical which may in part fragment further. U.S. Pat. No. 4,380,629 discloses styryl-like compounds that undergo coloration or bleaching, reversibly or irreversibly, via ring-opening and ring-closing in response to activating energies. U.S. Pat. No. 4,720,449 describes an intramolecular acylation reaction that converts a colorless molecule to a colored form. U.S. Pat. No. 4,243,052 describes pyrolysis of a mixed carbonate of a quinophthalone precursor that may be used to form a dye. U.S. Pat. No. 4,602,263 describes a thermally-removable protecting group that may be used to reveal a dye or to change the color of a dye. U.S. Pat. No. 5,350,870 describes an intramolecular acylation reaction that may be used to induce a color change. A further example of a unimolecular color-forming reaction is described in "New Thermo-Response Dyes: Coloration by the Claisen Rearrangement and Intramolecular Acid-Base Reaction Masahiko Inouye, Kikuo Tsuchiya, and Teijiro Kitao, Angew. Chem. Int. Ed. Engl. 31, pp. 204–5 (1992).

In all of the above-mentioned examples, control of the chemical reaction is achieved through the change in rate that occurs with changing temperature. Thermally-induced changes in rates of chemical reactions in the absence of phase changes may often be approximated by the Arrhenius equation, in which the rate constant increases exponentially as the reciprocal of absolute temperature decreases (i.e., as temperature increases). The slope of the straight line relating the logarithm of the rate constant to the reciprocal of the absolute temperature is proportional to the so-called "activation energy". The prior art compounds described above are coated in an amorphous state prior to imaging, and thus no change in phase is expected or described as occurring between room temperature and the imaging temperature. Thus, as employed in the prior art, these compounds exhibit strongly time-dependent coloration temperatures. Some of these prior art compounds are described as having been isolated in crystalline form. Nevertheless, in no case is there mentioned in this prior art any change in activation energy of the color-forming reaction that may occur when crystals of the compounds are melted.

Other prior art thermal imaging media depend upon melting to trigger image formation. Typically, two or more chemical compounds that react together to produce a color change are coated onto a substrate in such a way that they are segregated from one another, for example, as dispersions of small crystals. Melting, either of the compounds themselves or of an additional fusible vehicle, brings them into contact with one another and causes a visible image to be formed. For example, a colorless dye precursor may form color upon heat-induced contact with a reagent. This reagent may be a Bronsted acid, as described in "Imaging Processes and Materials", Neblette's Eighth Edition, J. Sturge, V. Walworth, A. Shepp, Eds., Van Nostrand Reinhold, 1989, pp. 274–275, or a Lewis acid, as described for example in U.S. Pat. No. 4,636,819. Suitable dye precursors for use with acidic reagents are described, for example, in U.S. Pat. No. 2,417,897, South African Patent 68-00170, South African Patent 68-00323 and Ger. Offenlegungschrift 2,259,409. Further examples of such dyes may be found in "Synthesis and Properties of Phthalide-type Color Formers", by Ina Fletcher and Rudolf Zink, in "Chemistry and Applications of Leuco Dyes", Muthyala Ed., Plenum Press, New York, 1997. The acidic material may for example be a phenol derivative or an aromatic carboxylic acid derivative. Such thermal imaging materials and various combinations thereof are now well known, and various methods of preparing heat-sensitive recording elements employing these materials also are well known and have been described, for example, in U.S. Pat. Nos. 3,539,375, 4,401,717 and 4,415,633.

Prior art systems in which at least two separate components are mixed following a melting transition suffer from the drawback that the temperature required to form an image in a very short time by a thermal print-head may be substantially higher than the temperature required to colorize the medium during longer periods of heating. This difference is caused by the change in the rate of the diffusion needed to mix the molten components together, which may become limiting when heat is applied for very short periods. The temperature may need to be raised well above the melting points of the individual components to overcome this slow rate of diffusion. Diffusion rates may not be limiting during long periods of heating, however, and the temperature at which coloration takes place in these cases may actually be less than the melting point of either individual component, occurring at the eutectic melting point of the mixture of crystalline materials.

Despite the many prior art examples of direct thermal imaging systems, therefore, there are none in which the temperature of image formation is substantially time-independent. In particular, there has not previously been described a method for producing an image in which a crystalline chemical compound is converted to a liquid, or amorphous, form, the liquid form having intrinsically a different color from the crystalline form.

SUMMARY OF THE INVENTION

It is therefore an object of this invention to provide a novel imaging method.

Another object of the invention is to provide a thermal imaging method wherein the temperature at which an image is formed is time independent.

It is another object to provide an imaging method wherein an image is formed by converting a solid chemical compound in the crystalline form, at least partially, to a liquid in the amorphous form.

Still another object is to provide a multicolor thermal imaging method wherein at least one color separation image is formed by converting a solid chemical compound in the crystalline form at least partially to a liquid in the amorphous form.

Yet another object of the invention is to provide novel imaging members.

Another object of the invention is to provide a method for the manufacture of a direct thermal imaging member.

According to one aspect of the invention there are provided imaging methods wherein a chemical compound in a crystalline form is converted, at least partially, and preferably substantially completely or completely, to a liquid in the amorphous form, the liquid having intrinsically a different color from the crystalline form. The conversion to the liquid form can be carried out by applying heat to the thermal imaging member by any of the techniques known in thermal imaging such as from a thermal print head, a laser, a heated stylus, etc. In another embodiment, the conversion to the liquid form may be effected by applying a solvent ink jet for the crystalline solid such as from an imaging apparatus to at least partially dissolve the crystalline material. In another embodiment, one or more thermal solvents, which are crystalline materials, can be incorporated in the thermal imaging member. The crystalline thermal solvent(s), upon being heated, melt and dissolve or liquefy, and thereby convert, at least partially, the crystalline image-forming material to the liquid amorphous form to form the image. The conversion of the crystalline form to the liquid or amorphous form upon heating or dissolving the crystalline compounds of the present invention may produce a material of high or low viscosity. Typically, liquid or amorphous materials with viscosities higher than $10^{12}$ Pa·s are referred to as glasses. It may be that melting of the crystalline form produces a free-flowing liquid that, upon cooling, becomes a glass. The temperature at which the viscosity reaches $10^{12}$ Pa·s upon cooling is referred to as the glass transition temperature, or $T_g$. In order to form an image having a desirable degree of stability, it is preferred that recrystallization of the liquid or amorphous form into the crystalline form not occur. It is more likely that recrystallization will be slow when the liquid or amorphous form is a glass, i.e., at a temperature below its Tg. For this reason it is preferred that the Tg of the liquid or amorphous form of the compounds of the present invention be substantially above room temperature. Preferred Tg's are about 50° C. or greater In another aspect of the invention there are provided novel thermal imaging members. The thermal imaging members of the invention generally comprise a substrate carrying at least one image-forming layer including a compound in the crystalline form, which can be converted, as described previously, at least partially to a liquid in the amorphous form, the liquid having intrinsically a different color from the crystalline form. The thermal imaging member may be monochrome or multicolor and the temperature at which an image is formed in at least one of the image-forming layers is time independent.

The multicolor thermal imaging members of the invention may include at least one image-forming layer including a compound in the crystalline form, which can be converted, as described previously, at least partially to a liquid in the amorphous form, the liquid having intrinsically a different color from the crystalline form and at least one image-forming layer including materials which form a color by a different mechanism.

Preferred thermal imaging members according to the invention are those having the structures described in commonly assigned U.S. Pat. No. 6,537,410 B2, which is hereby incorporated herein by reference in its entirety and made a part of this application.

Other preferred thermal imaging members are those having the structures described in prior, co-pending commonly assigned U.S. patent application Ser. No. 10/151,432 filed May 20, 2002 (Patent Application Publication No. US2003/0125206) which is hereby incorporated herein by reference in its entirety and made a part of this application.

Further preferred thermal imaging members are those having the structures described in U.S. Pat. No. 6,054,246 which is hereby incorporated herein by reference in its entirety and made a part of this application.

In another aspect of the invention there is provided a method for manufacturing the thermal imaging members of the invention. Generally, the method includes the steps of forming a dispersion of the crystalline solid and optionally a binder, in a solvent in which the compound is insoluble or only sparingly soluble by any suitable method such as by grinding, attriting, etc. and forming a layer of the image-forming material on a substrate by any suitable method such as, for example, by coating the fluid onto the substrate using any of the techniques well-known in the coating art. These include slot, gravure, Mayer rod, roll, cascade, spray, and curtain coating techniques. The image-forming layer so formed is optionally overcoated with a protective layer or layers.

BRIEF DESCRIPTION OF THE DRAWINGS

For a better understanding of the invention as well as other objects and advantages and further features thereof, reference is made to the following detailed description of various preferred embodiments thereof taken in conjunction with the accompanying drawings wherein.

DETAILED DESCRIPTION OF THE INVENTION

Compounds in the crystalline state commonly have properties, including color, that are very different from those of the same compounds in an amorphous form. In a crystal, a molecule is typically held in a single conformation (or, more rarely, in a small number of conformations) by the packing forces of the lattice. Likewise, if a molecule can exist in more than one interconverting isomeric forms, only one of such isomeric forms is commonly present in the crystalline state. In amorphous form or solution, on the other hand, the compound may explore its whole conformational and isomeric space, and only a small proportion of the population of individual molecules of the compound may at any one time exhibit the particular conformation or isomeric form adopted in the crystal. These phenomena are exploited in three similar ways in the compositions, imaging methods and imaging members of the present invention.

Figure 1:
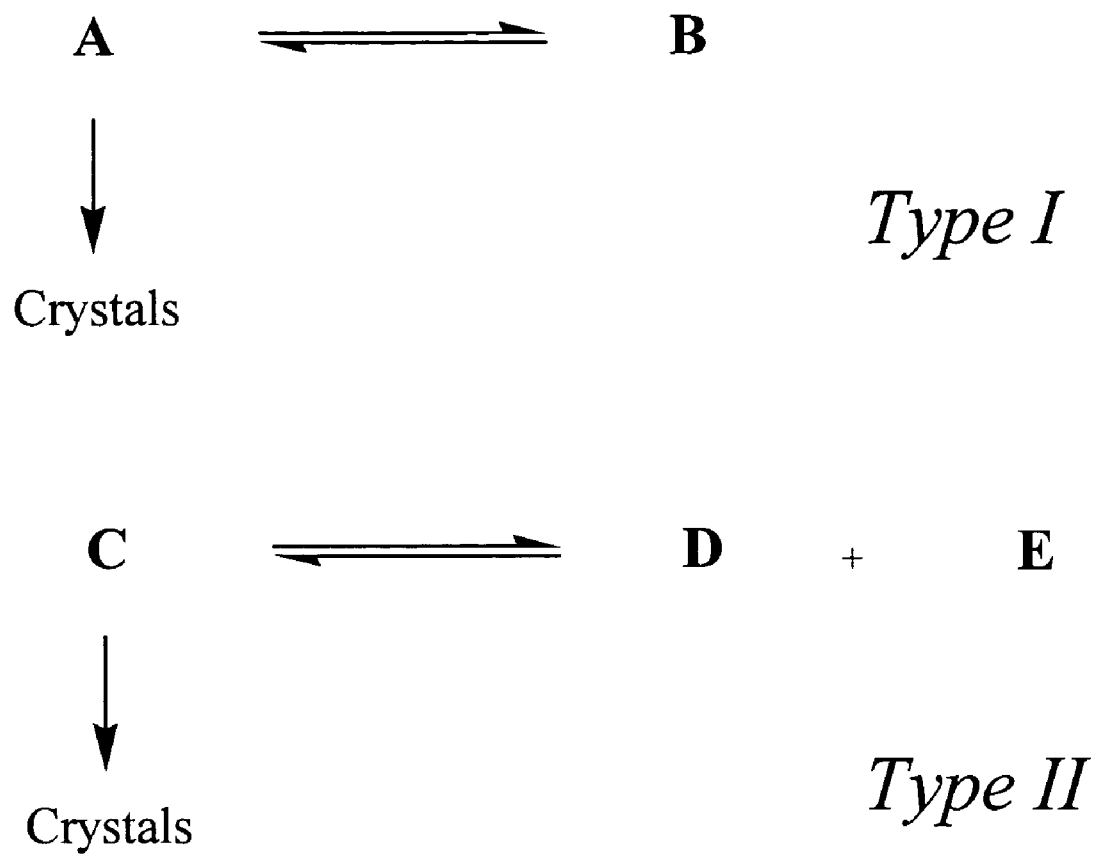
FIG. 1 illustrates two different chemical mechanisms, Types I and II, by which images can be formed according to the present invention.

Referring now to FIG. 1, there are seen two types of chemical equilibria which are exploited according to the present invention, designated Types I and II. The first type takes advantage of the fact that certain dye molecules exhibit tautomerism in solution (i.e., they exist as different, interconverting isomers at equilibrium). This is shown in FIG. 1, Type I, as the equilibrium between interconverting chemical entities A and B. Only two chemical species are shown in FIG. 1, Type I, but this is for the sake of simplicity only, and is not intended to limit the scope of invention in any way. The discussion provided herein applies equally to any number of interconverting tautomers. In the crystalline state, as described above, only one of the possible tautomeric forms will usually be present. Thus, crystallization of the mixture of A and B can produce crystals of pure A, or pure B, depending upon the conditions used.

Different tautomers may have different electronic structures from one another, and therefore different absorption of electromagnetic radiation. It is not unusual, therefore, for different tautomers to have different colors. The equilibrium distribution of tautomers will depend upon the polarity of the medium in which they are dissolved. Thus, a polar tautomer will be favored in a polar medium, while a less polar tautomer will be favored in a less polar medium. If a dye molecule exhibiting tautomerism can be crystallized into a single tautomeric form, the crystalline state will exhibit the color of that particular tautomer. If such a crystalline form is heated and converted to the liquid form or dissolved in a solvent, the tautomeric equilibrium will be re-established, so that at least some of the tautomer or tautomers not present in the crystal will be present, in relative amounts dependent upon the polarity of the molten state or solution. Since contributions from tautomers not present in the crystal will be seen, the color of the melt or solution is likely to be different from that of the crystal.

According to the invention, there have been identified molecules exhibiting tautomerism in which at least one tautomeric form is colorless, and at least another tautomeric form is colored. This is represented in FIG. 1, Type I, provided that molecule A is colorless, and molecule B is colored. Crystallization of the equilibrating mixture of A and B is carried out so as to produce colorless crystals of pure A. The solvent chosen to perform the crystallization will typically be one of such polarity (and other chemical properties, such as hydrogen-bonding ability) that A is favored, either in the equilibrium between A and B in solution, or in having lower solubility in the solvent than B. The choice of solvent is usually determined empirically for a particular mixture of tautomers.

Upon conversion of the pure crystalline A, the equilibrium between tautomers A and B is re-established in the resulting amorphous (liquid) phase. The proportion of the amorphous material that is colored (i.e., the proportion that is in the B tautomeric form) may vary, but is preferably at least about 10%.

The colored and colorless tautomeric forms of the molecules of the present invention must meet certain criteria for image quality and permanence. The colorless form, which it is preferred be the crystalline form, should have minimal visible absorption. It should be stable to light, heating below the melting point, humidity, and other environmental factors such as ozone, oxygen, nitrogen oxides, fingerprint oils, etc. These environmental factors are well known to those skilled in the imaging art. The colored, amorphous form should be stable also to the above mentioned conditions, and in addition should not recrystallize to the colorless form under normal handling conditions of the image. The colored form should have a spectral absorption appropriate for digital color rendition. Typically, the colored form should be yellow (blue-absorbing), magenta (green-absorbing), cyan (red absorbing), or black, without undue absorption in an unintended spectral region. For nonphotographic applications, however, it may be required that the colored form not be one of the subtractive primary colors, but rather a particular spot color (for example, orange, blue, etc.).

The thermal imaging members of the invention can be direct thermal imaging members wherein an image is formed in the member itself or they can be thermal transfer imaging members whereby image-forming material is transferred to an image-receiving member. The melting point of the molecules used in direct thermal imaging members of the present invention is preferably in the range of about 60° C. to about 300° C. Melting points lower than about 60° C. lead to direct thermal imaging members that are unstable to temperatures occasionally encountered during handling of the members before or after imaging, while melting temperatures above about 300° C. render the compounds difficult to colorize with a conventional thermal print head. It should be noted, however, that there are uses for certain novel compounds of the present invention that do not require the use of thermal print heads (for example, laser imaging).

The multicolor thermal imaging members of the invention include those wherein all the color-forming layers are carried on the same side of a substrate as well as those wherein at least one color-forming layer is carried on a first side of a substrate and at least one color-forming layer is carried on a second side of the substrate.

Figure 2:
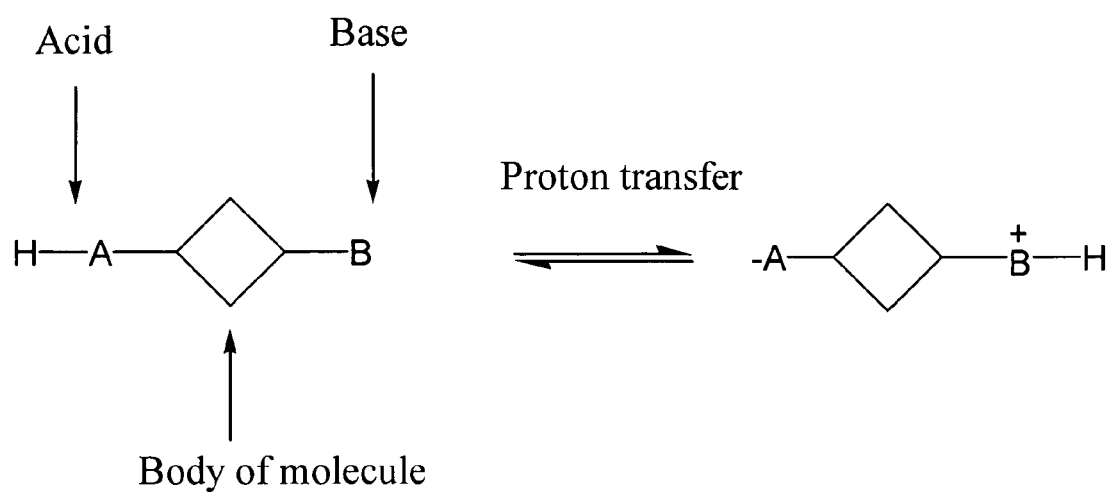
FIG. 2 illustrates a proton transfer equilibrium characteristic of materials which undergo the Type I mechanism shown in FIG. 1.

A preferred tautomeric equilibrium of the present invention involves proton transfer. As shown in FIG. 2, a molecule containing an acidic and a basic site can exist either in the protonated acid and unprotonated base tautomeric form, or in the unprotonated acid and protonated base form. These two forms can have different colors if either the acidic site or the basic site of the molecule constitute an indicator dye. Thus, the molecule might consist of a colorless, basic indicator dye (that becomes colored in the presence of an acid) covalently joined to an acid, or a colorless, acidic indicator dye (that becomes colored when deprotonated) covalently joined to a base. Of course, the molecule may also consist of a basic indicator dye covalently joined to an acidic indicator dye. The strengths of the acidic and the basic sites must be such that an equilibrium may be established that does not overwhelmingly favor one of the two tautomers under most conditions. This is most easily achieved if the acid and the base are weak. An especially preferred acidic grouping is a phenol, while the basic site may vary widely, commonly being an electronegative heteroatom such as oxygen or nitrogen.

Preferred examples of tautomeric molecules of Type I of the present invention include the following xanthene derivatives. Two tautomeric forms of the xanthene derivatives are shown (represented by formulae I and II), but this is not meant to exclude additional tautomeric forms of the molecule. (It should be noted that only one of the possible tautomers of xanthene

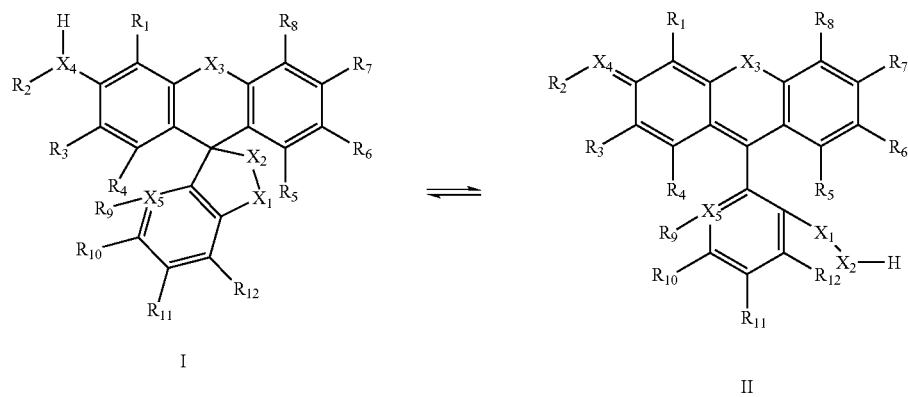

I  II molecules is sometimes reported in the literature.)

wherein $R_1$, $R_3$, $R_4$, $R_5$, $R_6$, and $R_8$ are each independently hydrogen, alkyl, aryl, halogen, or substituted or unsubstituted oxygen, nitrogen or sulfur atoms;

$R_2$ is hydrogen, alkyl, aryl, or is absent;

$R_7$ is substituted or unsubstituted oxygen, nitrogen, sulfur, or halogen;

$R_9$, $R_{10}$, $R_{11}$ and $R_{12}$ are each independently hydrogen, alkyl, aryl, halogen, nitro or substituted or unsubstituted oxygen, nitrogen or sulfur atoms, or absent;

$X_1$ is carbonyl, methylene, or sulfonyl;

$X_2$ is oxygen or nitrogen, substituted with hydrogen, alkyl, aryl, or nitrogen;

$X_3$ and $X_4$ are each independently oxygen, sulfur, or nitrogen; and $X_5$ is carbon or nitrogen.

In these compounds, the acidic grouping of formula I comprises the group $X_4$ bearing the hydrogen atom, and the basic site of formula I comprises the atom $X_2$. Transfer of a proton from $X_4$ to $X_2$ gives a compound of formula II.

One preferred subgroup of xanthenes of formula I are fluorescein compounds, wherein $X_4$ is oxygen and $R_7$ is oxygen substituted with hydrogen, alkyl or aryl; and $X_1$ is carbonyl; $X_2$ is oxygen; and $X_3$ is oxygen.

Many fluorescein derivatives of the above subtype are known in the art. One tautomeric form (corresponding to formula I) of such compounds is colorless (absorbing in the ultraviolet region of the electromagnetic spectrum), whereas a second tautomeric form (corresponding to formula II) is often yellow in color. Fluorescein itself is the compound of formula I, in which $R_2$ is absent, $R_7$ is a hydroxyl group, $R_1$, $R_3$, $R_4$, $R_5$, $R_6$, $R_8$, $R_9$, $R_{10}$, $R_{11}$ and $R_{12}$ are each hydrogen atoms, $X_1$ is carbonyl, $X_2$, $X_3$ and $X_4$ are each oxygen and $X_5$ is carbon. It has been found that there are difficulties with many of these prior art compounds. Fluorescein itself is difficult to crystallize in a colorless form and in the amorphous form exhibits complex equilibria including several, differently colored species. A simplification may be made if $R_7$ is an ether grouping. Thus, the previously known compound benzyl fluorescein, in which the substituents are as described above for fluorescein itself except that $R_7$ is a benzyloxy group, is readily crystallized into a colorless form. The amorphous form of benzyl fluorescein has a yellow color.

Benzyl fluorescein has the disadvantage that only a small proportion of the amorphous form (about 4%) is colored (i.e., about 96% of the amorphous form is in the tautomeric form corresponding to formula I, and about 4% in the structure corresponding to formula II). It has been found that much higher proportions of the colored tautomer in the amorphous form may be obtained when at least two of $R_1$, $R_3$, $R_6$ and $R_8$ in formula I comprise an alkyl substituent, as described in more detail in Example 1 below.

Especially preferred fluorescein derivatives of the present invention are derivatives of formula I in which at least two of $R_1$, $R_3$, $R_6$ and $R_8$ comprise an alkyl group having between one and about twelve carbon atoms, which may be branched or linear, and which may comprise aryl or heteroatomic substituents, $R_2$ is absent, $R_4$, $R_5$, $R_9$, $R_{10}$, $R_{11}$ and $R_{12}$ are each hydrogen, $R_7$ is an ether grouping, $X_1$ is a carbonyl group, $X_2$, $X_3$ and $X_4$ are each oxygen and $X_5$ is carbon.

Specific preferred compounds of formula I are those in which $R_2$ is absent, $R_4$, $R_5$, $R_9$, $R_{10}$, $R_{11}$ and $R_{12}$ are each hydrogen, $X_1$ is carbonyl, $X_2$, $X_3$ and $X_4$ are each oxygen, $X_5$ is carbon, and the other substituents are as follows:

Compound F-1: $R_1$ and $R_8$ are each hydrogen, $R_3$ and $R_6$ are each n-hexyl and $R_7$ is benzyloxy;

Compound F-2: $R_1$ and $R_8$ are each hydrogen, $R_3$ and $R_6$ are each n-hexyl and $R_7$ is ethoxy;

Compound F-3: $R_1$ and $R_8$ are each hydrogen, $R_3$ and $R_6$ are each ethyl and $R_7$ is benzyloxy;

Compound F-4: $R_1$ and $R_8$ are each hydrogen, $R_3$ and $R_6$ are each n-hexyl and $R_7$ is ethoxy;

Compound F-5: $R_1$ and $R_8$ are each methyl, $R_3$ and $R_6$ are each hydrogen and $R_7$ is benzyloxy;

Compound F-6: $R_1$ and $R_8$ are each methyl, $R_3$ and $R_6$ are each hydrogen and $R_7$ is 2-methoxyethoxy;

Compound F-7: $R_1$ and $R_8$ are each hydrogen, $R_3$ and $R_6$ are each ethyl and $R_7$ is 3-methylbut-1-oxy;

Compound F-8: $R_1$ and $R_8$ are each hydrogen, $R_3$ and $R_6$ are each ethyl and $R_7$ is 2-methylbenzyloxy;

Compound F-9: $R_1$ and $R_8$ are each hydrogen, $R_3$ and $R_6$ are each ethyl and $R_7$ is 3-methylbenzyloxyt;

Compound F-10: $R_1$ and $R_8$ are each hydrogen, $R_3$ and $R_6$ are each benzyl and $R_7$ is benzyloxy;

Compound F-11: $R_1$ and $R_8$ are each hydrogen, $R_3$ and $R_6$ are each propyl, and $R_7$ is benzyloxy; and Compound F-12: $R_1$ and $R_8$ are each hydrogen, $R_3$ and $R_6$ are each benzyl and $R_7$ is 3-methylbut-1-oxy.

Certain of compounds F-1 through F-12 are novel compounds described and claimed in commonly assigned U.S. patent application Ser. No. 10/789,566, filed on even date herewith, the entire disclosure of which is hereby incorporated by reference herein and made a part of this application.

A second preferred subgroup of xanthenes of formula I are rhodol-type compounds, wherein $X_4$ is oxygen, $R_2$ is absent and $R_7$ is nitrogen bearing two substituents each of which may independently be hydrogen, alkyl or aryl; $X_1$ is carbonyl; and $X_2$, $X_3$ and $X_4$ are each oxygen.

Preferred compounds of the rhodol type are those in which $R_1$ is hydrogen, halogen, or alkyl; $R_2$ is absent; $R_3$ is an electron-withdrawing substituent such as halogen, sulfonyl or nitro; $R_7$ is nitrogen bearing at least one aryl substituent; $R_4$, $R_5$, $R_6$, $R_8$, $R_9$, $R_{10}$, $R_{11}$ and $R_{12}$ are each hydrogen; $X_1$ is carbonyl; $X_2$, $X_3$ and $X_4$ are each oxygen; and $X_5$ is carbon. It has been found that rhodol-type compounds can afford good magenta (green-absorbing) chromophores provided that $R_3$ is an electron-withdrawing substituent such as a halogen, sulfonyl or nitro and $R_7$ is nitrogen bearing at least one aryl substituent. Absent the electron-withdrawing substituent at $R_3$, or the aryl substituent on the nitrogen atom at $R_7$, the wavelength of absorption is shorter, and the colored tautomer of the molecule exhibits a red, rather than a magenta, color.

Specific preferred rhodol-type compounds of formula I are those in which $R_2$ is absent; $R_4$, $R_5$, $R_6$, $R_8$, $R_9$, $R_{10}$, $R_{11}$ and $R_{12}$ are each hydrogen; $X_1$ is carbonyl; $X_2$, $X_3$ and $X_4$ are each oxygen; $X_5$ is carbon; and the other substituents are as follows:

Compound Rh-1: $R_1$ is hydrogen, $R_3$ is bromine and $R_7$ is phenylamino;

Compound Rh-2: $R_1$ is hydrogen, $R_3$ is bromine and $R_7$ is N-ethyl-N-phenylamino;

Compound Rh-3: $R_1$ is hydrogen, $R_3$ is bromine and $R_7$ is N-butyl-N-phenylamino;

Compound Rh-4: $R_1$ is hydrogen, $R_3$ is bromine and $R_7$ is N-hexyl-N-phenylamino;

Compound Rh-5: $R_1$ is hydrogen, $R_3$ is bromine and $R_7$ is N-benzyl-N-phenylamino;

Compound Rh-6: $R_1$ is hydrogen, $R_3$ is bromine and $R_7$ is N,N-diphenylamino;

Compound Rh-7: $R_1$ is methyl, $R_3$ is bromine and $R_7$ is N-hexyl-N-phenylamino;

Compound Rh-8: $R_1$ is hydrogen, $R_3$ is hydrogen and $R_7$ is N-indolinyl; and Compound Rh-9: $R_1$ is hydrogen, $R_3$ is bromine and $R_7$ is N-hexadecyl-N-phenylamino.

Certain of the compounds Rh-1 through Rh-9 are novel compounds and are described and claimed in commonly assigned U.S. patent application Ser. No. 10/789,276, filed on even date herewith, the entire disclosure of which is hereby incorporated by reference herein and made a part of this application.

A third preferred subgroup of xanthenes of formula I are rhodamine-type compounds, in which $R_1$, $R_3$, $R_4$, $R_5$, $R_6$, $R_8$, $R_9$, $R_{10}$, $R_{11}$ and $R_{12}$ are each hydrogen, alkyl, aryl or halogen, $R_2$ is hydrogen, alkyl or aryl and $R_7$ is nitrogen bearing two substituents each of which independently may be hydrogen, alkyl or aryl, or oxygen bearing an alkyl or aryl substituent; $X_1$ is carbonyl; $X_2$ is oxygen; $X_3$ is oxygen; $X_4$ is nitrogen; and $X_5$ is carbon.

Specific preferred rhodamine-type compounds of formula I are those in which $R_1$, $R_3$, $R_4$, $R_5$, $R_6$, $R_8$, $R_9$, $R_{10}$, $R_{11}$ and $R_{12}$ are each hydrogen; $X_1$ is carbonyl; $X_2$ and $X_3$ are each oxygen; $X_4$ is nitrogen; $X_5$ is carbon; and the other substituents are as follows:

Compound R-1: $R_2$ is phenyl and $R_7$ is phenylamino;

Compound R-2: $R_2$ is 2-methylphenyl and $R_7$ is 2-methylphenylamino;

Compound R-3: $R_2$ is 2-ethylphenyl and $R_7$ is 2-ethylphenylamino;

Compound R-4: $R_2$ is 2,4,6-trimethylphenyl and $R_7$ is 2,4,6-trimethylphenylamino;

Compound R-5: $R_2$ is 2-chlorophenyl and $R_7$ is 2-chlorophenylamino.

Another specific preferred rhodamine-type compound of formula I is Compound R-6, in which $R_1$, $R_3$, $R_4$, $R_5$, $R_6$, and $R_8$ are each hydrogen, $R_2$ is a 2-methyl-4-octadecyloxyphenyl group, $R_7$ is an N-indolinyl group, $R_9$, $R_{10}$, $R_{11}$ and $R_{12}$ are each fluorine, $X_1$ is carbonyl, $X_2$ and $X_3$ are each oxygen, $X_4$ is nitrogen, and $X_5$ is carbon.

Certain of the compounds R-1 through R-6 are novel compounds and are described and claimed in commonly assigned U.S. patent application Ser. No. 10/788,963, filed on even date herewith, the entire disclosure of which is hereby incorporated by reference herein and made a part of this application.

Two problems commonly occur in designing molecules for use according to the mechanism of Type I. Firstly, it may turn out to be impossible to crystallize the colorless tautomeric form of the molecule. For example, many of the rhodol-type compounds described above cannot readily be crystallized in a colorless form. Secondly, the colorless form may be able to be crystallized, but may exhibit a non-ideal melting point. To change the melting point would require complete redesign of the molecule, a long and tedious process. However, as described in U.S. Pat. No. 4,097,288, it is well known that certain phenolic or amino compounds readily form co-crystals with hydrogen-bonding acceptors or donors. Such hydrogen-bonding acceptors or donors are hereinafter referred to as "complexing agents". A co-crystal of a given molecule of the present invention in conjunction with a hydrogen-bonding complexing agent does not necessarily have the same melting point as either the complexing agent or the molecule of the present invention on its own.

As mentioned above, in each of the preferred types of formula I, atom $X_4$ bears a hydrogen substituent. This hydrogen atom, besides being the internal acid used to produce the colored tautomeric form of the molecule, is also available to be complexed by a hydrogen-bonding acceptor. Complexation, as described above, not only may enable crystallization of the colorless tautomeric form of the molecule in cases where this would otherwise be difficult to achieve, but may also allow control of the melting point. Preferred complexing agents are amino compounds, especially heterocyclic materials such as pyridines. Specific preferred complexing agents include phenanthroline, 2,9-dimethylphenanthroline, 4,5,6,7-tetramethylphenanthroline, methyl picolinate, ethyl picolinate, pyrazine, 4,4'-bispyridine, 2,2'-bispyridine, terephthalamides such as N,N,N',N'-tetramethylterephalamide and the corresponding tetrabutyl derivative, and cyclic oxalamides such as 1,4-dimethyl-2,3-dioxopiperazine. Example 4 below illustrates the effect of complexation to crystallize the colorless tautomeric form of rhodol-type compounds used in the present invention and to tailor the melting point of these and other molecules of the present invention.

Novel complexes which are useful in the imaging members and methods of the invention are described and claimed in commonly assigned U.S. patent application Ser. No. 10/789,600, filed on even date herewith, the entire disclosure of which is hereby incorporated by reference herein and made a part of this application.

Figure 3:
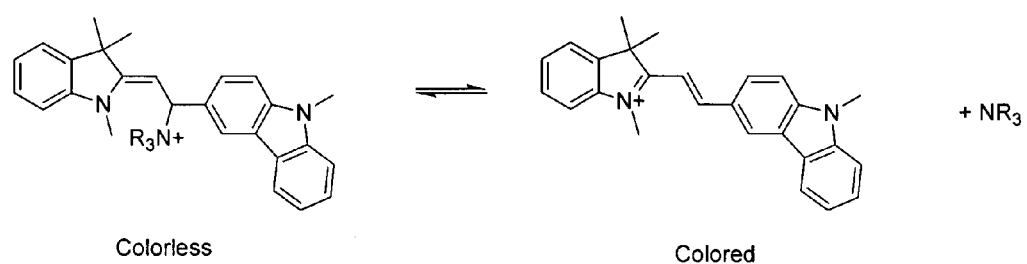
FIG. 3 illustrates a chemical mechanism characteristic of materials which undergo the Type II mechanism.
Figure 3:
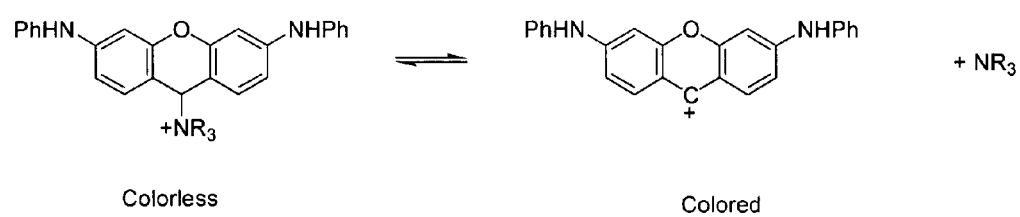

The present invention is not limited to compounds that exist in different tautomeric forms. In a second embodiment of the invention, illustrated in FIG. 1, Type II, the equilibrium established is between a colorless adduct, shown as C, and its two constituents, shown as D and E. D is a colored dye, while E is a colorless molecule that can add to D and render it colorless. Typically, D is a cationic dye (an electrophile) and E is a nucleophile. During crystallization of C, the concentration of E may be made sufficiently high (and much higher than that of D) that very little of D is present. When D is melted, however, the concentration of D and E will be the same. The position of the equilibrium may thus be different in the amorphous form resulting from melting of C than it was in the solution from which C was crystallized in the first place. FIG. 3 shows two examples of equilibria that can be used for Type II of the present invention. Scheme 1 of FIG. 3 shows the equilibrium between a hemicyanine dye and a colorless adduct formed by addition of a tertiary amine. Scheme 2 shows a similar equilibrium established between a xanthene dye and a tertiary amine. A wide variety of nucleophilic molecules may be used to establish equilibria such as those shown in FIG. 3, but it is preferred that the adduct formed between the dye and the nucleophile have the same charge as the final dye. If this is not the case, for example if the adduct is neutral but the dye is positively charged, in order to maintain charge balance the nucleophile in the dissociated state must be negatively charged. In this case, it is likely that the nucleophile will remain closely associated with the dye due to electrostatic attraction. The adduct and the dye will both be positively charged if the dye is positively charged and the nucleophile is a tertiary amine, a tertiary phosphine, or a thioether, for example.

To form a direct thermal imaging system, the crystalline, colorless form of the compound of Types I and II described above is made into a dispersion in a solvent in which the compound is insoluble or only sparingly soluble, by any of the methods known in the art for forming dispersions. Such methods include grinding, attriting, etc. The particular solvent chosen will depend upon the particular crystalline material. Solvents that may be used include water, organic solvents such as hydrocarbons, esters, alcohols, ketones, nitriles, and organic halide solvents such as chlorinated and fluorinated hydrocarbons. The dispersed crystalline material may be combined with a binder, which may be polymeric. Suitable binders include water-soluble polymers such as poly(vinyl alcohol), poly(vinylpyrollidone) and cellulose derivatives, water-dispersed latices such as styrene/butadiene or poly(urethane) derivatives, or alternatively hydrocarbon-soluble polymers such as polyethylene, polypropylene, copolymers of ethylene and norbornene, and polystyrene. This list is not intended to be exhaustive, but is merely intended to indicate the breadth of choice available for the polymeric binder. The binder may be dissolved or dispersed in the solvent.

Following preparation of the dispersion of the compound of the present invention, and optional addition of a polymeric binder, the resultant fluid is coated onto a substrate using any of the techniques well-known in the coating art.

These include slot, gravure, Mayer rod, roll, cascade, spray, and curtain coating techniques. The image-forming layer so formed is optionally overcoated with a protective layer or layers.

Where materials of the present invention are used to prepare an imaging medium of the type described in copending U.S. patent application Ser. No. 10/151,432 filed May 20, 2002 the process described above is followed for each of the imaging layers. Successive layers may be coated sequentially, in tandem, or in a combination of sequential and tandem coatings.

EXAMPLES

The invention will now be described further in detail with respect to specific embodiments by way of examples, it being understood that these are intended to be illustrative only and the invention is not limited to the materials, amounts, procedures and process parameters, etc. recited therein. All parts and percentages recited are by weight unless otherwise specified.

Example 1

This example describes the preparation and properties of novel fluorescein derivatives of formula I.

A. Novel fluorescein derivatives were prepared in the following general manner (exemplified by the preparation of Compound F-11).

Preparation of 4-propyl-1,3-dihydroxybenzene.

i. 1,3-Dihydroxy-4-propanoylbenzene (10 g; 60.2 mmol) and trifluoroacetic acid (10 eq., 0.6 mol; 68.4 g) were stirred at room temperature until all the material was dissolved. To the resultant solution there was added triethylsilane (2.5 eq., 0.15 mol; 17.5 g) slowly at room temperature. After the addition, the reaction mixture was stirred with heating at 75° C. for 4 hours. The mixture was cooled to room temperature, quenched into water and extracted with dichloromethane to give two layers of oil product. The upper layer (excess triethylsilane) was decanted off and to the residual oil product there was added a mixture of hexane and dichloromethane (ca. 7:3 ratio) with heating to give a solid product. The product (7.3 g; 80% yield), whose structure was confirmed by $^1$H NMR and Electrospray mass spectrometry (ES MS) was used for the next step without further purification.

ii. Preparation of 2,7-dipropylfluorescein.

To a mixture of 4-propyl-1,3-dihydroxybenzene (6.0 g; 40 mmol, prepared as described in (i) above) and phthalic anhydride (20 mmol; 3.0 g) there was added 73% (w/w) concentrated sulfuric acid at room temperature and the mixture was then stirred with heating at 150° C. for 3 hours. After cooling, the mixture was poured into water (200 mL) with stirring in the beaker, filtered, and washed with water several times to give yellow product with a quantitative yield. The structure of the product was confirmed by $^1$H NMR and ES MS.

iii. Preparation of Compound F-11.

2,7-Dipropylfluorescein (3 g; 7.2 mmol, prepared as described in (ii) above) and anhydrous potassium carbonate (4 eq., 28.8 mmol) were dispersed in dimethylformamide (DMF, 35 mL) at room temperature and the mixture was then stirred with heating at 100° C. until reddish clear solution appeared. To the resultant solution was added benzyl bromide (4 eq., 28.8 mmol; 4.9 g) dissolved in DMF (5 mL) slowly for 10 min. After the addition had been completed the mixture was further stirred at 100° C. for another 3 hours. After cooling the mixture to room temperature it was poured into water (400 mL) to give a precipitate. The crude product, (monoether, monoester) was hydrolyzed without further purification. The monoether monoester product was dissolved in a mixture of acetone (60 mL) and water (20 mL) and to this solution there was added aqueous sodium hydroxide (4 eq., 28.8 mmol; 1.2 g; 12 mL a 10% aqueous solution). The mixture was stirred at room temperature overnight. After evaporation of acetone the mixture was diluted with water (200 mL) and filtered. The filtrate was neutralized with dilute hydrochloric acid to give pale yellow precipitate. The crude product was purified by silica gel column chromatography (eluted with 3% methanol in dichloromethane) followed by recrystalization from a mixture of hexane and acetone to give colorless crystals (1.75 g, 48% yield, mp 202–203° C.).

B. The fluorescein derivatives so prepared, having structures described hereinabove, exhibited the following properties:

| Compound | Color of melt | Melting point (° C.) | Melting Range (° C.) |
|---|---|---|---|
| F-1 | Yellow | 111* | — |
| F-2 | Yellow | 225* | — |
| F-3 | Yellow | 230* | — |
| F-4 | Yellow | 107 | 7.2 |
| F-5 | Orange | 220* | — |
| F-6 | Orange | 251 | 5.4 |
| F-7 | Yellow | 194 | 5.0 |
| F-8 | Yellow | 115* | — |
| F-9 | Yellow | 160* | — |
| F-10 | Yellow | 219 | 4.6 |
| F-11 | Yellow | 210 | 5.3 |
| F-12 | Yellow | 207 | 4.6 |

Unless indicated by (*), melting points were determined by differential scanning calorimetry (DSC) at a temperature ramp rate of 4° C./min.
*Indicates that melting points were obtained using a capillary melting point apparatus.

Unless indicated by (*), melting points were determined by differential scanning calorimetry (DSC) at a temperature ramp rate of 4° C./min. (*) Indicates that melting pints were obtained using a capillary melting point apparatus.

Example 2

This example describes the preparation of novel rhodol-type derivatives of the invention Derivatives Rh-1-Rh-7 were prepared in the following general manner (exemplified by Rh-7 ia. Preparation of 2-(5-bromo-2,4-dihydroxybenzoyl)benzoic acid (starting material for Rh-1-Rh-6 and Rh-9).

Aluminum chloride (8.48 g, 64 mmol) was added to a stirring suspension of phthalic anhydride (2.36 g, 16 mmol) in tetrachloroethane (40 mL) under nitrogen. Nitromethane (6 mL) was added to dissolve the reactants. 4-Bromoresorcinol (3 g, 16 mmol) was added and the mixture continued to stir under nitrogen. The reaction was monitored by high performance liquid chromatography (HPLC) over a period of 2 hours. It was observed that the reaction had ceased within the first 30 minutes, with starting materials remaining. The solution was diluted with ethyl acetate (~150 mL) and washed with 1M hydrochloric acid (2×100 mL). The product was extracted from the organic layer into a saturated solution of sodium bicarbonate in water (200 mL). The basic aqueous phase was acidified with 3M hydrochloric acid to a pH of 5. The product was extracted from the aqueous phase into ethyl acetate (150 mL), washed with brine (2×100 mL), dried over magnesium sulfate and concentrated to give an orange oil which solidified upon standing for about 10 minutes. The solid was slurried in dichloromethane (20 mL) and filtered to give a mixture of the desired product and phthalic acid. Slurrying in water (20 mL) followed by filtration gave the desired product as a beige powder (1.72 g, 5.1 mmol, 32% yield).

ib. Alternative Preparation, Illustrated for 2-(5-bromo-2,4-dihydroxy-3-methylbenzoyl)benzoic acid (starting material for Rh-7).

Step 1: Aluminum chloride (21.4 g, 161 mmol) was added to a stirring suspension of phthalic anhydride (6 g, 40 mmol) in tetrachloroethane (200 mL) under nitrogen. 1,3-Dihydroxy-2-methylbenzene (5 g, 40 mmol) was added and the mixture quickly thickened. After the precipitates were broken up with a spatula the reaction continued for 1 hour. The solution was diluted with ethyl acetate (~600 mL) and washed with 1M hydrochloric acid (2×200 mL). The product was extracted from the organic layer into a saturated solution of sodium bicarbonate in water (600 mL). The basic aqueous phase was acidified with 3M hydrochloric acid to a pH of 5. The product was extracted from the aqueous phase into ethyl acetate (400 mL), washed with brine (2×100 mL), dried over magnesium sulfate and concentrated to give a brownish solid. The solid was slurried in dichloromethane (20 mL) and filtered to give 2-(2,4-dihydroxy-3-methylbenzoyl)benzoic acid as an off white powder (4.6 g, 16.9 mmol, 42% yield).

Step 2: Bromine (2.6 g, 16.9 mmol) was dripped into a stirring solution of the product from Step 1 (4.6 g=16.9 mmol) dissolved in acetic acid (42 mL). Monitoring by HPLC showed complete bromination within 1 hour. The solution was concentrated to give a yellow powder. Slurrying in dichloromethane followed by filtration gave the desired product as an off white powder (5 g, 14.3 mmol, 85% yield).

ii. Preparation of Compound Rh-7.

2-(5-Bromo-2,4-dihydroxybenzoyl)benzoic acid (prepared as described in ia above, 1 g, 2.86 mmol) was dissolved in acetic acid (14 mL). N-hexyl-N-(3-hydroxyphenyl)phenylamine (0.77 g, 2.86 mmol) was added to the solution followed by methanesulfonic acid (8.58 mmol). The solution was stirred at reflux for 4 hours. The solution was diluted with ethyl acetate (100 mL), washed with water (2×50 mL), a pH 7 phosphate buffer (2×30 mL) and brine (2×30 mL), dried over anhydrous magnesium sulfate and concentrated to a dark purple solid. Purification by silica gel column chromatography eluted the product with 5% acetone in dichloromethane (0.75 g, 1.28 mmol, 45% yield, $\lambda_{max}$=548 nm). The structure of the product was confirmed by $^1$H NMR and ES MS.

Other rhodol derivates were prepared in an analogous manner:

Rh-1: 3.08 g of 2-(5-bromo-2,4-dihydroxybenzoyl)benzoic acid and 1.69 g of 3-hydroxydiphenylamine afford 3.45 g (76% yield) of Compound Rh-1.

Rh-2: 1.5 g of 2-(5-bromo-2,4-dihydroxybenzoyl)benzoic acid and 1.0 g of N-ethyl-N-(3-hydroxyphenyl)phenylamine were reacted to afford 1.78 g (77% yield) of Compound Rh-2.

Rh-3: 418 mg of 2-(5-bromo-2,4-dihydroxybenzoyl)benzoic acid and 300 mg of N-butyl-N-(3-hydroxyphenyl)phenylamine were reacted to afford 401 mg (59% yield) of Compound Rh-3.

Rh-4: 1.0 g of 2-(5-bromo-2,4-dihydroxybenzoyl)benzoic acid and 0.83 g of N-hexyl-N-(3-hydroxyphenyl)phenylamine were reacted to afford 1.2 g (71% yield) of Compound Rh-4.

Rh-5: 413 mg of 2-(5-bromo-2,4-dihydroxybenzoyl)benzoic acid and 340 mg of N-benzyl-N-(3-hydroxyphenyl) phenylamine were reacted to afford 343 mg (59% yield) of Compound Rh-5.

Rh-6: 2-(5-Bromo-2,4-dihydroxybenzoyl)benzoic acid and N-phenyl-N-(3-hydroxyphenyl)phenylamine were reacted to afford 0.410 gms (15% yield) of Compound Rh-6 ($\lambda_{max}$=542 nm)

Rh-9: 467 mg of 2-(5-bromo-2,4-dihydroxybenzoyl)benzoic acid and 480 mg of N-hexadecyl-N-(3-hydroxyphenyl) phenylamine were reacted to afford 435 mg (44% yield) of Compound Rh-9.

Example 3

This example describes the preparation and properties of novel rhodamine-type derivatives. General procedure (exemplified for Compound R-2):

A mixture of dichlorofluoran (5.55 g, 15 mmol), o-toluidine (5.2 g, 48 mmol), anhydrous zinc chloride (4.5 g) and zinc oxide (1.5 g) was stirred at 200° C. for 1.5 hours. The still-hot reaction mixture was then quenched with stirring into 8% hydrochloric acid solution (300 mL) and stirred at 90° C. for 30 minutes, then filtered. The filter cake was washed with water (100 mL), dried, and dissolved in warm methanol (100 mL). The solution was made basic by addition of a solution of concentrated ammonia solution (7 mL) in methanol (15 mL), then quenched with stirring into cold water (700 mL). The slurry was filtered, and the filter cake was washed with water (150 mL) and dried overnight under reduced pressure to give a dark purple solid (22 g). This material was triturated with hot methylene chloride (100 mL) and filtered. The filtrate was purified by column chromatography on silica gel with dichloromethane/methanol as eluant. The slightly impure resulting material was further purified by recrystallization from toluene to give pale purple prisms (2.6 g). The solids from the dichloromethane trituration were heated with refluxing toluene (25 mL), filtered hot, diluted with heptane (20 mL), cooled to 20° C., and filtered to give a further 1.2 g of pale purple prisms. The residual solids from the toluene hot filtration were taken up in refluxing xylenes (15 mL) and cooled to deposit an additional 1.0 g of pale purple solid.

Compounds R1–R5 exhibited the following properties. In most cases, solvent of crystallization was incorporated into the crystals.

| Compound | Solvent of crystallization | Melting point (capillary, ° C.) | $\lambda_{max}$ (methanol, nm) |
|---|---|---|---|
| R1 | None | 268 | 544 |
| R2 | Toluene | 170 | 526 |
| R2 | Dichloromethane | 147 | 526 |
| R3 | Dichloromethane | 117 | 526 |
| R4 | Dichloromethane | 184 | 522 |
| R5 | Toluene | 122 | 520 |

Example 4

This example describes the preparation and properties of complexed materials.

General Procedure A:

The complexing agent (1.0 or 0.5 equivalents) was combined with the color forming agent and dissolved in an appropriate blend of hot methyl ethyl ketone and cyclohexane. When successful, the complex crystallized from the hot solution as it cooled as colorless or nearly colorless crystals. The crystals were collected by suction filtration and washed with an appropriate blend of methyl ethyl ketone/cyclohexane. This wash must be carefully done to avoid the precipitation of colored materials on the surface of the crystals. Analysis by $^1$H NMR spectroscopy defined the composition of the complex. Integral ratios of 1:1 and 2:1 of dye to complexing agent were most commonly observed and depended both on the structure of the dye and the structure of the complexing agent.

General Procedure B:

The complexing agent (1.0 or 0.5 equivalents) and color forming agent were combined and ground with an agate mortar and pestle. The resulting intimate mixture was then slurried on the mortar in a small amount of cyclohexane and the grinding was continued. Small amounts of methyl ethyl ketone were then added to facilitate dissolution of the components into the solvent and aid crystal growth. The grinding was continued until a colorless complex was formed. Often the stronger solvent (methyl ethyl ketone) was allowed to slowly evaporate during the grinding process until a critical concentration was achieved. At this point crystallization often proceeded. Once crystallization had occurred additional cyclohexane/methyl ethyl ketone was added and the slurry of crystals was transferred either to a container for further ripening (heating and stirring) or directly collected by suction filtration. The crystals were then carefully washed with an appropriate mixture of cyclohexane/methyl ethyl ketone to avoid precipitating colored dye on the surface of the crystals. Crystals from this procedure could be used to seed crystallizations using procedure A.

| Dye | Complexing Agent | Procedure | Ratio | m.p. (DSC, ° C.) |
|---|---|---|---|---|
| Benzylfluorescein | 1,10-phenanthroline | A | 1:1 | 201 |
| Benzylfluorescein | 2,9-Dimethyl-1,10-phenanthroline | A | 1:1 | 185 |
| Benzylfluorescein | 4,4'-bipyridyl | A | 2:1 | 109 |
| Benzylfluorescein | Pyrazine | A | 1:1 | 125* |
| Benzylfluorescein | Ethylpicolinate | A | 1:1 | 138 |
| F-3 | 4,4'-bipyridyl | B | 2:1 | 191 |
| F-4 | 4,4'-bipyridyl | B | 2:1 | 215 |
| F-9 | 4,4'-bipyridyl | B | 2:1 | 165 |
| F-10 | 4,4'-bipyridyl | B | 2:1 | 198 |
| Rh-1 | 2,9-Dimethyl-1,10-phenanthroline | A | 1:2 | 244* |
| Rh-1 | 4,4'-bipyridyl | A | 1:1 | 187 |
| Rh-2 | 4,4'-bipyridyl | B | 2:1 | 210 |
| Rh-4 | 2,9-Dimethyl-1,10-phenanthroline | A | 1:1 | 109 |
| Rh-4 | 2,9-Dimethyl-1,10 phenanthroline | B | 1:1 | 108 |
| Rh-4 | 4,4'-bipyridyl | B | | 160 |
| Rh-6 | 4,4'-bipyridyl | B | 2:1 | 260 |
| Rh-8 | 4,4'-bipyridyl | A | 2:1 | 180 |
| Rh-8 | 2,9-Dimethyl-1,10-phenanthroline | A | 1:1 | 142 |
| Rh-8 | Cyclic Oxalamide | A | 1:2 | 145 |

(*indicates capillary melting point.)

Example 5

This example illustrates thermal imaging members and thermal imaging methods according to the invention. The thermal imaging members provide yellow (imaging members 5A and 5B) and magenta (imaging member 5C) colors.

The following materials were used in this example:

Topas 8007, a copolymer of ethylene and norbornene, available from Ticona, 90 Morris Avenue, Summit, N.J. 07901;

Airvol 540, a grade of poly(vinyl alcohol) available from Air Products and Chemicals, Inc., Allentown, Pa.;

Zonyl FSA, a surfactant, available from DuPont Corporation, Wilmington, Del.;

Hymicron ZK-349, a grade of zinc stearate available from Cytech Products, Inc., Elizabethtown, Ky.;

Klebosol 30V-25, a silica dispersion available from Clariant Corporation, Muttenz, Switzerland;

Glyoxal, available from Aldrich Chemical Co., Milwaukee, Wis.;

Melinex 534, a white poly(ethylene terephthalate) film base of approximately 96 microns' thickness, available from DuPont Teijin Films U.S. Limited Partnership, 1 Discover Drive, P.O. Box 411, Hopewell, Va.

A. An image-forming layer was prepared as follows:

A compound of the present invention (0.15 g) was dispersed in a mixture comprising Topas 8007 (0.15 g of a 10% solution in methylcyclohexane) and methylcyclohexane (1.2 g), using an attriter equipped with glass beads, stirred for 18 hours at room temperature. The total solid content of the resulting dispersion was 11%.

The above dispersion was used to make the coating fluid for the dye-forming layer in proportions stated below. The coating composition thus prepared was coated onto Melinex 534 using a #18 Mayer rod, and dried. The intended coating thickness was 3.9 microns.

| Ingredient | % solids in dried film |
|---|---|
| Dispersion | 1.5 g |
| 10% Topas 8007/methylcyclohexane | 0.493 g |
| Methylcyclohexane | 0.15 g |

B. A barrier layer was coated onto the imaging layer by applying a 10% solution of Topas 8007 in methylcyclohexane using a #12 Mayer rod, for an intended thickness of approximately 2.6 microns.

C. A slip overcoat was coated on the barrier layer. The overcoat was prepared in proportions stated below. The overcoat coating composition applied using a #18 Mayer rod for an intended thickness of 1.6 microns.

| Ingredient | % solids in dried film |
| --- | --- |
| Glyoxal | 9.59% |
| Hymicron ZK-349 | 31.42% |
| Klebosol 30V-25 | 23.53% |
| Zonyl FSA | 3.89% |
| Airvol 540 | 31.57% |

The resulting imaging member was printed using a laboratory test-bed printer equipped with a thermal head, model KYT106-12PAN13 (Kyocera Corporation, 6 Takedatobadono-cho, Fushimi-ku, Kyoto, Japan).

The following printing parameters were used:

| | |
| --- | --- |
| Printhead width: | 4 inches |
| Pixels per inch: | 300 |
| Resistor size: | 70 × 80 microns |
| Resistance: | 4047 Ohm |
| Line Speed: | 7 milliseconds per line |
| Pressure: | 1.5–2 lb/linear inch |
| Dot pattern: | Rectangular grid. |

The following results were obtained from imaging members prepared using:

Imaging Member 5A: benzyl fluorescein (mp 191° C.);

Imaging Member 5B: a novel fluorescein compound of the present invention (F-11, mp 210° C.); and Imaging Member 5C: a novel complex of the present invention prepared from the novel rhodol-type compound Rh-4 and 2,9-dimethyl-1,10-phenanthroline (mp 109° C.).

| Imaging Member 5A | | | |
| --- | --- | --- | --- |
| Voltage = 14 V Energy (J/cm$^2$) | Density (blue) | Voltage = 16 V Energy (J/cm$^2$) | Density (blue) |
| 4.01 | 0.07 | 5.24 | 0.51 |
| 3.61 | 0.06 | 4.72 | 0.31 |
| 3.21 | 0.04 | 4.19 | 0.15 |
| 2.81 | 0.04 | 3.67 | 0.08 |
| 2.41 | 0.01 | 3.14 | 0.07 |
| 2.01 | 0.04 | 2.62 | 0.04 |
| 1.61 | 0.04 | 2.10 | 0.04 |
| 1.20 | 0.04 | 1.57 | 0.04 |
| 0.80 | 0.04 | 1.05 | 0.04 |
| 0.40 | 0.04 | 0.52 | 0.04 |
| 0.00 | 0.04 | 0.00 | 0.04 |

| Imaging Member 5B | | | |
| --- | --- | --- | --- |
| Voltage = 14 V Energy (J/cm$^2$) | Density (blue) | Voltage = 16 V Energy (J/cm$^2$) | Density (blue) |
| 4.01 | 0.13 | 5.24 | 1.1 |
| 3.61 | 0.1 | 4.72 | 1.03 |
| 3.21 | 0.08 | 4.19 | 0.71 |
| 2.81 | 0.08 | 3.67 | 0.42 |
| 2.41 | 0.07 | 3.14 | 0.16 |
| 2.01 | 0.07 | 2.62 | 0.1 |
| 1.61 | 0.07 | 2.10 | 0.07 |
| 1.20 | 0.07 | 1.57 | 0.06 |
| 0.80 | 0.07 | 1.05 | 0.07 |
| 0.40 | 0.07 | 0.52 | 0.06 |
| 0.00 | 0.06 | 0.00 | 0.06 |

| Imaging Member 5C | | | |
| --- | --- | --- | --- |
| Voltage = 14 V Energy (J/cm$^2$) | Density (green) | Voltage = 16 V Energy (J/cm$^2$) | Density (green) |
| 4.01 | 0.67 | 5.24 | 0.51 |
| 3.61 | 0.48 | 4.72 | 0.48 |
| 3.21 | 0.52 | 4.19 | 0.7 |
| 2.81 | 0.42 | 3.67 | 0.47 |
| 2.41 | 0.28 | 3.14 | 0.53 |
| 2.01 | 0.19 | 2.62 | 0.34 |
| 1.61 | 0.11 | 2.10 | 0.29 |
| 1.20 | 0.1 | 1.57 | 0.17 |
| 0.80 | 0.1 | 1.05 | 0.09 |
| 0.40 | 0.09 | 0.52 | 0.08 |
| 0.00 | 0.09 | 0.00 | 0.09 |

The following conclusions may be drawn:

a. The density with no printing energy applied was, for the three imaging members, 0.04, 0.06 and 0.09, indicating that the unmelted crystalline dispersions coated to form the color-forming layer were initially substantially colorless;

b. The maximum densities achieved for the three imaging members were, respectively, 0.51, 1.1 and 0.7. As described above, the only active components in the three color-forming layers were benzyl fluorescein, F-11, and the complex formed between Rh-4 and 2,9-dimethyl-1,10-phenanthroline, respectively. No developers or other chemical adjuvants were present. Therefore, the color formed must have arisen through intrinsic color change of these materials.

c. For imaging members A and B, whose melting points were 191° C. and 210° C., respectively, imaging occurred when 16V was applied to the print head whereas very little color change was observed with 14 V applied. On the other hand, for imaging member C, with melting point 109° C., substantial color change was observed under both 16V and 14V printing conditions. The amount of energy applied during printing at 14V is lower than that applied while printing at 16V, and consequently the temperature achieved in the color-forming layer is lower for 14V printing than for 16 V printing. Whether or not color is formed can therefore be concluded to depend upon the melting point of the color-forming layer and the temperature of heating.

d. The maximum density achieved in Imaging Member A (0.51) is lower than that achieved in Imaging Member B (1.1). Imaging Member A comprises benzyl fluorescein, a known compound, whereas Imaging Member B comprises F-11, a preferred, novel, fluorescein derivative of the invention.

Example 6

This example illustrates a thermal imaging member and thermal imaging method according to the invention. The thermal imaging member provides a cyan color.

In addition to the materials described in Example 5 above, the following materials were used in this example:

Piccotac 1115, available from Eastman Chemical Company, 100 North Eastman Road, P. O. Box 511, Kingsport, Tenn.;

Melinex 6265, a white poly(ethylene terephthalate) film base of approximately 96 microns' thickness, available from DuPont Teijin Films U.S. Limited Partnership, 1 Discover Drive, P.O. Box 411, Hopewell, Va.

A. An image-forming layer was prepared as follows:

Compound R-6 of the present invention (0.08 g) was dispersed in a mixture comprising Topas 8007/Piccotac 1115 (ratio 1:1.25, 0.08 g of a 10% solution in methylcyclohexane) and methylcyclohexane (0.76 g), using an attriter equipped with glass beads, and stirred for 18 hours at room temperature. The total solid content of the resulting dispersion was 10%.

The above dispersion was used to make the coating fluid for the dye-forming layer in proportions stated below. The coating composition thus prepared was coated onto Melinex 6265 using a #9 Mayer rod, and dried. The intended coating thickness was approximately 2 microns.

| Ingredient | % solids in dried film |
| --- | --- |
| Dispersion | 0.93 g |
| 10% Topas 8007:Piccotac 1115/methylcyclohexane | 1.63 g |
| Methylcyclohexane | 0.09 g |

B. A barrier layer was coated onto the imaging layer by applying a 10% solution of 1:1.25 Topas 8007/Piccotac 1115 in methylcyclohexane using a #12 Mayer rod, for an intended thickness of approximately 2.6 microns.

C. A slip overcoat was coated on the barrier layer. The overcoat was prepared in proportions stated below. The overcoat coating composition applied using a #18 Mayer rod for an intended thickness of 1.6 microns.

| Ingredient | % solids in dried film |
| --- | --- |
| Glyoxal | 9.59% |
| Hymicron ZK-349 | 31.42% |
| Klebosol 30 V-25 | 23.53% |
| Zonyl FSA | 3.89% |
| Airvol 540 | 31.57% |

The resulting imaging member was printed using a laboratory test-bed printer equipped with a thermal head, model KYT106-12PAN13 (Kyocera Corporation, 6 Takedatobadono-cho, Fushimi-ku, Kyoto, Japan).

The following printing parameters were used:

| Printhead width: | 4 inches |
| --- | --- |
| Pixels per inch: | 300 |
| Resistor size: | 70 × 80 microns |
| Resistance: | 4291 Ohm |
| Line Speed: | 7 milliseconds per line |
| Pressure: | 1.5–2 lb/linear inch |
| Dot pattern: | Rectangular grid. |

The following results were obtained:

| Voltage = 16.5 V Energy ($J/cm^2$) | Density (red) |
| --- | --- |
| 5.88 | 1.13 |
| 5.29 | 1.10 |
| 4.71 | 1.05 |
| 4.12 | 0.79 |
| 3.53 | 0.52 |
| 2.94 | 0.30 |
| 2.35 | 0.14 |
| 1.76 | 0.1 |
| 1.18 | 0.1 |
| 0.59 | 0.1 |
| 0.00 | 0.1 |

Example 7

This example illustrates a thermal imaging member comprising more than one color-forming layer, designed to be printed with a single thermal print-head as described in above-mentioned patent application Ser. No. 10/151,432. In this example the topmost layer, printed in a relatively short time at a relatively high temperature, comprises a material of the present invention. The lower layer, printed in a relatively long time at a relatively low temperature, comprises a prior art color-forming composition in which two compounds (a leuco dye and an acid developer) that react together to form color are brought together by melting and diffusing.

In addition to materials described in Examples 5 and 6 above, the following materials were used in this Example:

Leuco dye Red 40, 3,3-bis(1-n-butyl-2-methyl-indol-3-yl) phthalide (available from Yamamoto Chemical Industry Co., Ltd., Wakayama, Japan);

Acid Developer TGSA, bis(3-allyl-4-hydroxyphenyl)sulfone, available from Nippon Kayaku Co., Ltd, Tokyo, Japan;

Airvol 205, a grade of poly(vinyl alcohol) available from Air Products and Chemicals, Inc., Allentown, Pa.;

Airvol 325, a grade of poly(vinyl alcohol) available from Air Products and Chemicals, Inc., Allentown, Pa.;

Zonyl FSN, a surfactant, available from DuPont Corporation, Wilmington, Del.;

Elvacite 2045, a grade of poly(isobutyl methacrylate), available from Lucite International Inc., 7275 Goodlett Farms Parkway, Cordova, Tenn.;

Aerosol OT-100, a surfactant available from Cytec Industries, Inc., West Paterson, N.J.

A white, reflective layer was coated onto the back of a clear poly(ethylene terephthalate) substrate of 125 micron thickness (Cronar 512, available DuPont Teijin Films U.S. Limited Partnership, 1 Discover Drive, P.O. Box 411, Hopewell, Va.). The following layers were applied to the opposite side of the substrate:

A. Prior Art Color-Forming Layer, Affording a Magenta Color.

An aqueous dispersion of a magenta color-former (Red 40), poly(vinyl alcohol) (Airvol 205) and a surfactant (Zonyl FSN) was mixed with an aqueous dispersion of an acid developer (TGSA), poly(vinyl alcohol) (Airvol 205) and a surfactant (Zonyl FSN). A solution of poly(vinyl alcohol) binder (Airvol 540) in water was added and the resultant fluid was coated for a dried coverage of Red 40: 300 mg/m$^2$, TGSA 1139 mg/m$^2$, Zonyl FSN 13 mg/m$^2$, and combined poly(vinyl alcohol) (Airvol 205 and Airvol 540) 661 mg/m$^2$.

B. A Thermally-Insulating Interlayer.

A solution of Elvacite 2045 in methylcyclohexane was coated to a dried coverage of 8016 mg/m$^2$.

C. Yellow Color-Forming Layer of the Present Invention.

A dispersion of Compound F-11 of the present invention was prepared as follows:

Compound F-11 (600 g), surfactant Aerosol OT-100 (30 g), heptanes (1.1 kg) and ethyl acetate (600 g) were combined and transferred into a 1S-Attritor containing 6.3 kg mullite beads. The jacket temperature was set to 10° C. and the attritor was run at 100 rpm for 24 hours. The grinding media was filtered off and washed with heptanes (500 g). The resulting suspension of crystalline Compound F-11 was concentrated to dryness yielding 620 g of white solid. This solid was redispersed in an aqueous solution of poly(vinyl alcohol) (Airvol 540) containing a surfactant (Zonyl FSN) to produce a coating fluid, which was coated to a dried coverage of Compound F-11: 1184 mg/m$^2$, Aerosol OT-100: 59.2 mg/m$^2$, Airvol 540: 344 mg/m$^2$, and Zonyl FSN 11 mg/m$^2$.

D. An Oxygen Barrier Layer.

The following materials were coated from aqueous solution to give the indicated dried coverages:

poly(vinyl alcohol) (Airvol 325, 1454 mg/m$^2$), boric acid crosslinker (125 mg/m$^2$) and Zonyl FSN (32 mg/m$^2$)

E. A UV-Absorbing Barrier Layer.

An aqueous fluid was coated to provide the following dried coverages: nanoparticulate zinc oxide (UV absorber, 2153 mg/m$^2$), poly(vinyl alcohol) (Airvol 325, 1615 mg/m$^2$), Zonyl FSN (32 mg/m$^2$).

F. A Slip Coat.

An aqueous coating fluid was coated to give the following dried coverages: Hymicron ZK-349 (312 32 mg/m$^2$), Airvol 540 (635 32 mg/m$^2$), Klebosol 30V-25 (517 32 mg/m$^2$) and Zonyl FSN (32 32 mg/m$^2$).

The resulting imaging member was printed using a laboratory test-bed printer equipped with a thermal head, model KPT163 (Kyocera Corporation, 6 Takedatobadono-cho, Fushimi-ku, Kyoto, Japan).

The following printing parameters were used:

| | |
|---|---|
| Pixels per inch: | 300 |
| Resistor size: | 70 × 120 microns |
| Resistance: | 3135 Ohm |
| Line Speed: | 11.1 milliseconds per line |
| Pressure: | 1.5–2 lb/linear inch |
| Voltage: | 40.9 V |
| Dot pattern: | Rectangular grid. |

The time taken to print each line was divided into 667 equal time elements. Energy was supplied to the print head for a proportion of each of these time elements referred to as the "duty cycle". For high average power in printing, the duty cycle was a high proportion of the total duration of the time element, while for low average power the duty cycle was a low proportion of the total duration of the time element. Because of both the time taken for thermal diffusion and the large size of the resistor relative to the distance traveled by the imaging element during each time element, the thermal pulses of each of the time elements were not resolved as individual dots on the imaging element. Instead, the imaging element experienced an averaging of the power of the individual pulses.

The following results were obtained:

| High power, short time Duty cycle = 0.74 Time elements energised (667 maximum) | Density (blue) | Density (Green) |
|---|---|---|
| 0 | 0.155 | 0.17 |
| 16 | 0.195 | 0.172 |
| 18 | 0.259 | 0.18 |
| 20 | 0.399 | 0.202 |
| 23 | 0.621 | 0.239 |
| 25 | 0.799 | 0.277 |
| 27 | 0.936 | 0.306 |
| 29 | 1.095 | 0.343 |
| 32 | 1.221 | 0.386 |
| 34 | 1.30 | 0.433 |
| 36 | 1.326 | 0.425 |

| Low power, long time Duty cycle = 0.08 Time elements energised (667 maximum) | Density (blue) | Density (Green) |
|---|---|---|
| 0 | 0.156 | 0.173 |
| 250 | 0.187 | 0.192 |
| 292 | 0.205 | 0.225 |
| 335 | 0.226 | 0.303 |
| 377 | 0.266 | 0.467 |
| 419 | 0.33 | 0.725 |
| 462 | 0.418 | 1.065 |
| 504 | 0.518 | 1.361 |
| 546 | 0.627 | 1.597 |
| 589 | 0.69 | 1.679 |
| 631 | 0.693 | 1.703 |

It is readily apparent that in the high power, short time printing condition the blue density exceeds the green density (i.e., the yellow color predominates over the magenta color). In the low power, long time printing condition the green density exceeds the blue density (i.e., the magenta color predominates over the yellow color). The unwanted green density observed when printing yellow is mostly due to absorption of green light by the yellow dye. Likewise, the unwanted blue density observed while printing the magenta dye is mostly due to absorption of blue light by the magenta dye. Thus, Compound F-11 of the present invention can serve efficiently as an element in a thermal imaging member comprising more than one color-forming layer, designed to be printed with a single thermal print-head as described in above-mentioned patent application Ser. No. 10/151,432.

Example 8

This example illustrates the time-independence of the color-forming temperature of a thermal imaging member according to the invention.

The color-forming layer of Imaging Member A described in Example 5 above was subjected to heating using a thermal pressure laminator/sealer available from Sencorp Equipment, Hyannis, Mass. This device allows for the independent control of the time and temperature of heating of a sample. The optical densities (blue) obtained were as follows:

| Temperature | Time (seconds) | | | | |
|---|---|---|---|---|---|
| (° C.) | 0.01 | .1 | 1 | 10 | 90 |
| 188 | .49 | .59 | .47 | — | — |
| 182 | .35 | .58 | .55 | — | .28 |
| 177 | .36 | .29 | .35 | .41 | .19 |
| 166 | .11 | .08 | .09 | .08 | .18 |
| 160 | .04 | .06 | .04 | .05 | .07 |

It can be seen that over about four orders of magnitude in heating time, color change occurred between nominal 160 and nominal 177° C.

Although the invention has been described in detail with respect to various preferred embodiments thereof, it will be recognized by those skilled in the art that the invention is not limited thereto but rather that variations and modifications can be made therein which are within the spirit of the invention and the scope of the amended claims.

What is claimed is:

1. A color imaging member comprising a substrate bearing one or more color-forming layers, wherein at least one of said color-forming layers comprises a chemical compound in a crystalline form, said crystalline form being capable of being converted to an amorphous form, said chemical compound having intrinsically a different color in said crystalline form than in said amorphous form.

2. The imaging member as defined in claim 1 wherein the melting point of said chemical compound in said crystalline form is between about 60° C. and about 300° C.

3. The imaging member as defined in claim 1 in which the range of temperatures over which said chemical compound in said crystalline form melts is less than about 15° C.

4. The imaging member as defined in claim 1 wherein the Tg of said amorphous form of said chemical compound is about 50° C. or greater.

5. The imaging member as defined in claim 1 comprising at least two color-forming layers.

6. The imaging member as defined in claim 5 wherein a first color-forming layer comprises a first chemical compound in a crystalline form, and a second color-forming layer comprises a second chemical compound in a crystalline form, said crystalline forms of said first and second chemical compounds being capable of being converted to amorphous forms, said first and second chemical compounds having intrinsically different colors in said crystalline forms than in said amorphous forms.

7. The imaging member as defined in claim 1 comprising three color-forming layers.

8. The imaging member as defined in claim 7 wherein said color-forming layers form cyan, magenta and yellow, respectively.

9. The imaging member as defined in claim 7 wherein at least one of said color-forming layers is carried by a first side of said substrate and at least another of said color-forming layers is carried by a second side of said substrate.

10. The imaging member as defined in claim 9 wherein magenta and yellow color-forming layers are carried by said first side of said substrate and a cyan color-forming layer is carried by said second side of said substrate.

11. The imaging member as defined in claim 7 wherein said color-forming layers are initially substantially colorless.

12. The imaging member as defined in claim 1 wherein said color-forming layer comprising said chemical compound is initially substantially colorless.

13. A color imaging method comprising the steps of:
(a) providing an imaging member as defined in claim 1; and
(b) converting at least a portion of said chemical compound to an amorphous form in an imagewise pattern, whereby an image is formed.

14. The method as defined in claim 13 wherein step (b) comprises applying an imagewise pattern of thermal energy to said imaging member, said thermal energy being sufficient to convert at least some of said chemical compound to an amorphous form.

15. The method as defined in claim 14 wherein said imaging member includes at least two color-forming layers whereby a multicolor image is formed.

16. The method as defined in claim 15 wherein said imaging member includes three color-forming layers whereby a multicolor image is formed.

17. The method as defined in claim 16 wherein said color-forming layers form cyan, magenta and yellow, respectively.

18. The method as defined in claim 16 wherein at least one of said imaging wherein at least one of said color-forming layers is carried by a first side of said substrate and at least another of said color-forming layers is carried by a second side of said substrate.

19. The method as defined in claim 18 wherein magenta and yellow color-forming layers are carried by said first side of said substrate and a cyan color-forming layer is carried by said second side of said substrate.

20. The method as defined in claim 16 wherein said color-forming layers are initially colorless.

21. The method as defined in claim 15 wherein a first color-forming layer comprises a first chemical compound in a crystalline form, and a second color-forming layer comprises a second chemical compound in a crystalline form, said crystalline forms of said first and second chemical compounds being capable of being converted to amorphous forms, said first and second chemical compounds having intrinsically different colors in said crystalline forms than in said amorphous forms.

22. The method as defined in claim 13 wherein said color-forming layer comprising said chemical compound is initially colorless.

23. The method as defined in claim 13 wherein the melting point of said chemical compound in said crystalline form is between about 60° C. and about 300° C.

24. The method as defined in claim 13 wherein the range of temperatures over which said chemical compound in said crystalline form melts is less than about 15° C.

25. The method as defined in claim 13 wherein the Tg of the amorphous form of said chemical compound is about 50° C. or greater.

* * * * *